US 7,088,310 B2

(12) United States Patent
Sanford

(10) Patent No.: US 7,088,310 B2
(45) Date of Patent: *Aug. 8, 2006

(54) METHOD AND SYSTEM FOR PRESENTING AN IMAGE OF AN EXTERNAL VIEW IN A MOVING VEHICLE

(75) Inventor: William C. Sanford, Mukilteo, WA (US)

(73) Assignee: The Boeing Company, Seattle, WA (US)

( * ) Notice: Subject to any disclaimer, the term of this patent is extended or adjusted under 35 U.S.C. 154(b) by 35 days.

This patent is subject to a terminal disclaimer.

(21) Appl. No.: 10/427,677

(22) Filed: Apr. 30, 2003

(65) Prior Publication Data

US 2004/0217976 A1 Nov. 4, 2004

(51) Int. Cl.
*G09G 5/00* (2006.01)

(52) U.S. Cl. .......................................... 345/7; 348/148
(58) Field of Classification Search ............... 345/7, 345/8, 9; 348/148, 149, 117, 118, 208.3; 701/1, 3
See application file for complete search history.

(56) References Cited

U.S. PATENT DOCUMENTS

| 2,861,806 | A  | 11/1958 | Disney |
| 5,004,225 | A  | 4/1991  | Krukovsky |
| 5,253,051 | A  | 10/1993 | McManigal |
| 5,316,480 | A  | 5/1994  | Ellsworth |
| 4,937,751 | A1 | 1/2001  | Nimura |
| 5,610,822 | A1 | 1/2001  | Murphy |
| 6,443,913 | B1 | 1/2001  | Kania |
| 6,661,353 | B1 | 1/2001  | Gopen |
| 6,497,649 | B1 | 7/2002  | Parker |
| 6,538,622 | B1 | * 3/2003 | Kojima et al. .................. 345/7 |
| 6,545,601 | B1 | * 4/2003 | Monroe ....................... 340/521 |
| 6,714,141 | B1 | 10/2003 | Kennedy |
| 6,693,518 | B1 | * 2/2004 | Kumata et al. ............. 348/148 |
| 6,704,653 | B1 | 3/2004  | Kuriya et al. |
| 6,866,225 | B1 | * 3/2005 | Jones et al. .............. 244/118.5 |

(Continued)

OTHER PUBLICATIONS

Kaiser, Mary K. et al., "Dynamic Eye–Point Displays," (2 pages) http://vision.arc.nasa.gov/HST/Brief/Vision.S.T./Dynamic.E.html [Accessed Dec. 4, 2002].

O'Gara Aviation Company, "O'Gara Aviation Company is Proud to Offer For Sale: 1974 Dassault Breguet Falcon 20F–5BR, Serial No. 313, N184TS," <http://www.ogara-jets.com/aircraft_for sale/Falcon_20F_313/photos.htm>, [Accessed Oct. 4, 2005].

http://www.lexus.com/cpo/model_detail/is/430/2002.html; (4 pp.); accessed Aug. 16, 2004.

http://www.new–cars.com/2002/lexus/Is430/2002–lexus–is430–interior,ipq; (1 p.); accessed Aug. 16, 2004.

*Primary Examiner*—Matthew Luu
(74) *Attorney, Agent, or Firm*—Perkins Coie LLP

(57) ABSTRACT

Methods and systems for processing images corresponding to views external to a vehicle are disclosed. A system in accordance with one embodiment of the invention includes first and second signal receiving portions configured to receive a signal corresponding to an image of a view external to the vehicle and a speed of the vehicle, respectively. A signal processing portion can direct to a first display portion a first signal corresponding to the image and to a second display portion a second signal corresponding to the image, with the first and second display portions positioned at different locations of the vehicle. The second signal can be delayed by a time that corresponds at least approximately inversely to the speed of the vehicle. Accordingly, a viewer seeing both display portions can receive a visual indication that the vehicle is moving.

18 Claims, 8 Drawing Sheets

U.S. PATENT DOCUMENTS

| | | |
|---|---|---|
| 2002/0123829 A1 | 9/2002 | Kuriya |
| 2002/0183929 A1 * | 12/2002 | Tsuji et al. .................. 701/301 |
| 2003/0021445 A1 | 1/2003 | Larice et al. |
| 2003/0078713 A1 | 4/2003 | Tanaka |
| 2003/0083790 A1 | 5/2003 | Hattori |
| 2003/0107499 A1 * | 6/2003 | Lepere et al. ................ 340/945 |
| 2003/0179109 A1 | 9/2003 | Chamas |
| 2004/0051634 A1 * | 3/2004 | Schofield et al. ............ 348/148 |
| 2004/0189831 A1 * | 9/2004 | Shibatani et al. ...... 348/240.99 |

* cited by examiner

METHOD AND SYSTEM FOR PRESENTING AN IMAGE OF AN EXTERNAL VIEW IN A MOVING VEHICLE

CROSS-REFERENCE TO RELATED APPLICATIONS

The present application is related to and incorporates by reference the following U.S. Patent Applications, filed simultaneously herewith:

1. U.S. application Ser. No. 10/427,429 entitled METHOD AND SYSTEM FOR PRESENTING DIFFERENT VIEWS TO PASSENGERS IN A MOVING VEHICLE; and 2. U.S. application Ser. No. 10/427,405 entitled METHOD AND SYSTEM FOR PRESENTING MOVING SIMULATED IMAGES IN A MOVING VEHICLE.

TECHNICAL FIELD

The present invention relates to methods and systems for presenting images in moving vehicles, for example, presenting images of a region external to an aircraft to passengers within the aircraft.

BACKGROUND

Some vehicles provide occupants with limited visual access to the region exterior to the vehicle. For example, some trucks and buses provide limited visual access to the region directly behind the vehicle. One method for overcoming this drawback is to provide the vehicle with an aft-pointing camera that is connected to a display panel inside the vehicle. The display panel can accordingly present to the vehicle driver an image of what the driver would see if he or she were able to look through the rear of the vehicle. This system can therefore aid the driver as the driver backs up the vehicle or engages in other maneuvers that benefit from an aft-facing view. Another existing system includes a passenger aircraft seatback display that schematically portrays the aircraft superimposed on a map of the terrain the aircraft overflies. However, the foregoing systems can be limited because they present the same image to one or more viewers. Accordingly, the foregoing systems may not be adequate to provide multiple viewers at different positions within the vehicle with an accurate view of the external world outside the vehicle as the vehicle moves.

SUMMARY

The present invention is directed toward methods and systems for presenting to occupants of a moving vehicle an image of a view external to the vehicle. A system in accordance with one aspect of the invention includes a first signal receiving portion configured to receive a signal corresponding to an image of a view external to a vehicle, and a second signal receiving portion configured to receive a signal corresponding to a speed of the vehicle. A signal processing portion is configured to direct to a first display portion positioned at a first location of the vehicle a first signal corresponding to the image, and direct to a second display portion positioned at a second location of the vehicle a second signal corresponding to the image, with the second location being different than the first location. The signal processing portion is further configured to delay the second signal by a time that corresponds at least approximately inversely to the speed. Accordingly, in one aspect of the invention, passengers within a moving vehicle can receive time-delayed images that simulate what the passengers would see as their seats pass a fixed point.

In a further aspect of the invention, the vehicle can include an aircraft. In another aspect of the invention, the signal processing portion can be configured to synchronize the first and second signals when the aircraft is airborne. In still a further aspect of the invention, the vehicle can include first and second laterally spaced apart wheels, with a first speed sensor operatively coupled to the first wheel to detect its speed, and a second wheel sensor operatively coupled to the second wheel to detect its speed. Accordingly, the system can account for turning motions of the vehicle.

A method in accordance with another aspect of the invention includes receiving a signal corresponding to an image of a view external to a vehicle and receiving a signal corresponding to a speed of the vehicle. The method can further include directing to a first display portion positioned at a first location of the vehicle a first signal corresponding to the image, and directing to a second display portion positioned at a second location of the vehicle a second signal corresponding to the image, with the second location being spaced apart from the first location. The method can further include delaying the second signal by a time that corresponds at least approximately inversely to the speed. In further aspects of this method, the signal corresponding to the speed of the vehicle can include a signal corresponding to a linear speed of the vehicle and/or a rotational speed of the vehicle.

DETAILED DESCRIPTION

The present disclosure describes methods and systems for providing an image in a moving vehicle representative of a view outside the vehicle. Many specific details of certain embodiments of the invention are set forth in the following description and in FIGS. 1–8C to provide a thorough understanding of these embodiments. One skilled in the art, however, will understand that the present invention may have additional embodiments, and that the invention may be practiced without several of the details described below.

Embodiments of the invention can provide people inside a vehicle with a simulated, time-varying view of the region outside the vehicle, in a manner that is consistent with the motion of the vehicle. In one embodiment, the vehicle can include a passenger aircraft having few or no passenger windows. For purposes of illustration, aspects of the system are described in the context of a blended wing body aircraft. In other embodiments, the system can be incorporated into aircraft having other configurations, and/or vehicles other than aircraft.

Figure 1:
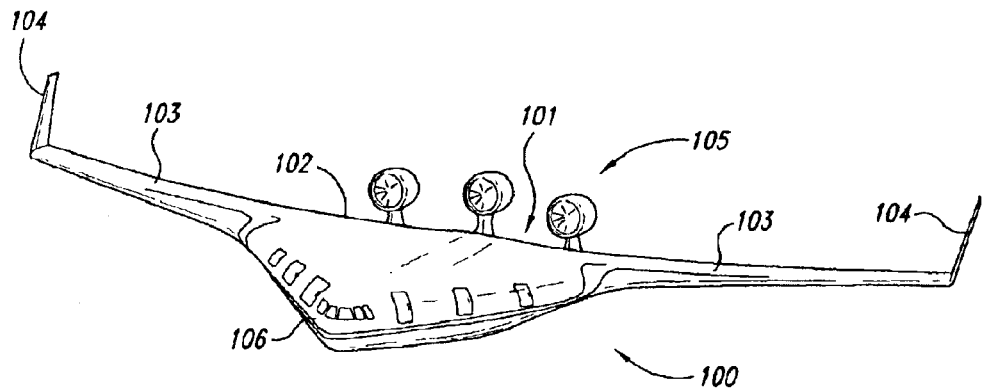
FIG. 1 is a partially schematic, front isometric illustration of an aircraft having a system for directing images of a view outside the aircraft to viewers within the aircraft in accordance with an embodiment of the invention.
Figure 2:
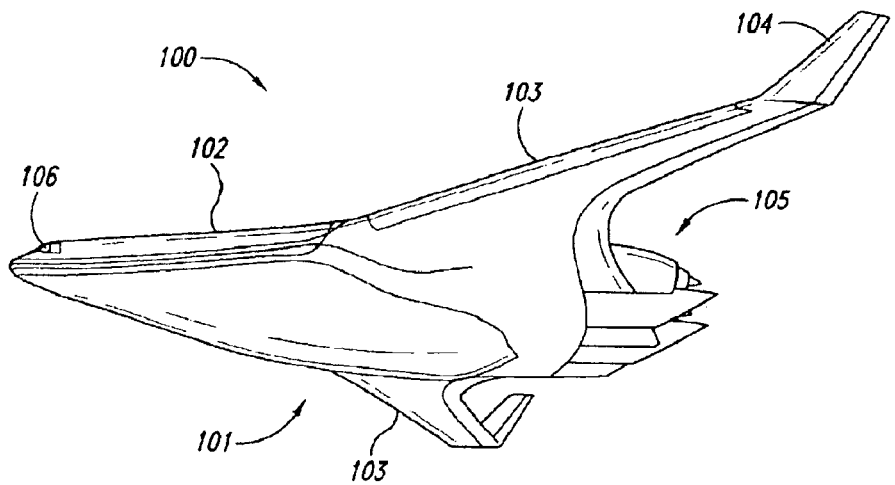
FIG. 2 is a partially schematic bottom isometric view of the aircraft shown in FIG. 1.

FIGS. 1 and 2 are partially schematic illustrations of an aircraft 100 having a blended wing body configuration in accordance with an embodiment of the invention. In one aspect of this embodiment, the aircraft 100 can include a blended wing body 101 having a central portion 102 for carrying a payload. Outboard portions 103 can extend laterally outwardly from the central portion 102. The aircraft 100 can include winglets 104 for lateral stability, and a propulsion system 105 for power. In one aspect of this embodiment, the propulsion system 105 can include three engines mounted above the upper surface of the blended wing body 101, and in other embodiments, the propulsion system 105 can have other arrangements. In any of these embodiments, the central portion 102 can include a forward-facing flight deck 106 from which the aircraft is operated.

Figure 3:
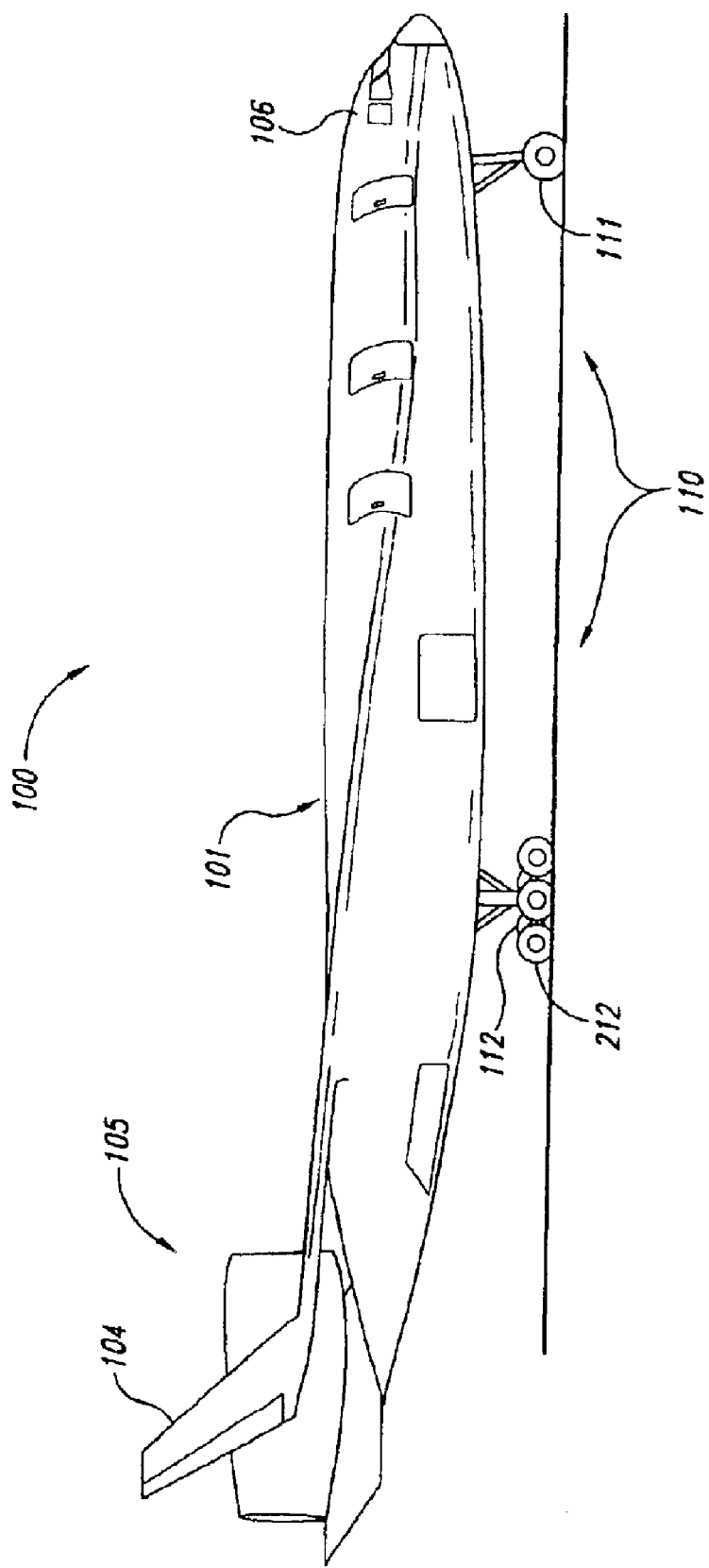
FIG. 3 is a partially schematic, side elevational view of the aircraft shown in FIG. 1.

FIG. 3 is a partially schematic, side elevational view of an embodiment of the aircraft 100 illustrating the blended wing body 101 supported on landing gear 110. The landing gear 110 can include a nose gear 111 and a plurality of main gears, for example, a left main gear 112 and a right main gear 212. In other embodiments, the aircraft 100 can have other landing gear configurations.

Figure 4:
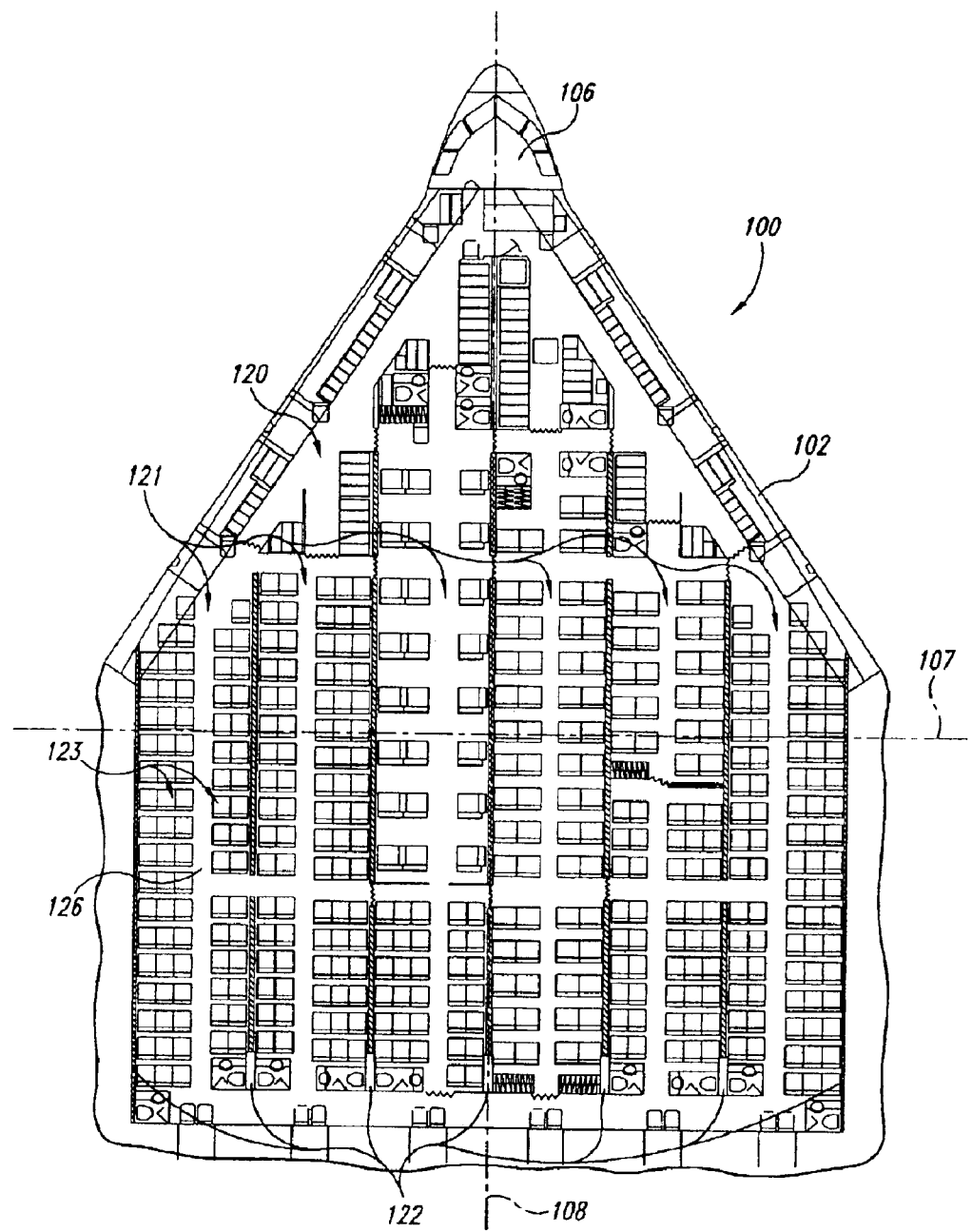
FIG. 4 is a partially schematic, top plan view of an interior of a portion of the aircraft shown in FIGS. 1–3, configured in accordance with an embodiment of the invention.

FIG. 4 is a partially schematic, top plan view of an interior portion of the aircraft 100, configured in accordance with an embodiment of the invention. In one aspect of this embodiment, the interior portion includes a passenger compartment 120 positioned aft of the flight deck 106. The passenger compartment 120 can be divided into a plurality of passenger bays 121 separated from each other by partitions 122. In a further aspect of this embodiment, each passenger bay 121 can be elongated in a direction generally parallel to a longitudinal axis or roll axis 108 of the aircraft 100. Each passenger bay 121 can house passenger seats 123 separated by aisles 126, which are also aligned generally parallel to the longitudinal axis 108. In other embodiments, the interior of the aircraft 100 can have other passenger seating arrangements. In any of these embodiments, the aircraft 100 can roll about the roll axis 108, and pitch about a pitch axis 107 during flight.

In any of the embodiments described above with reference to FIGS. 1–4, one characteristic of the aircraft 100 is that at least some of the seats 123 are not adjacent to a window and therefore passengers (not shown) in those seats do not have direct visual access to the region exterior to the aircraft 100. In fact, in at least one embodiment, the aircraft 100 can include few or no windows other than those at the flight deck 106. An advantage of a windowless (or reduced window) passenger compartment 120 is that it can allow for the efficient use of a relatively wide interior space, for example, the space provided by a blended wing body design. A further advantage is that eliminating or reducing the number of windows in the passenger compartment 120 can reduce the cost of manufacturing and/or maintaining the aircraft 100. However, the lack of windows may be uncomfortable for some passengers and may increase the likelihood that some passengers suffer from air sickness because they do not have access to visual cues that are consistent with the motion they feel. Accordingly, an embodiment of the invention described below with reference to FIGS. 5–8C includes a system and method for presenting to the passengers a series of images that are representative of the view external to the aircraft, and that appear to move consistently with the motion the passenger feels.

Figure 5:
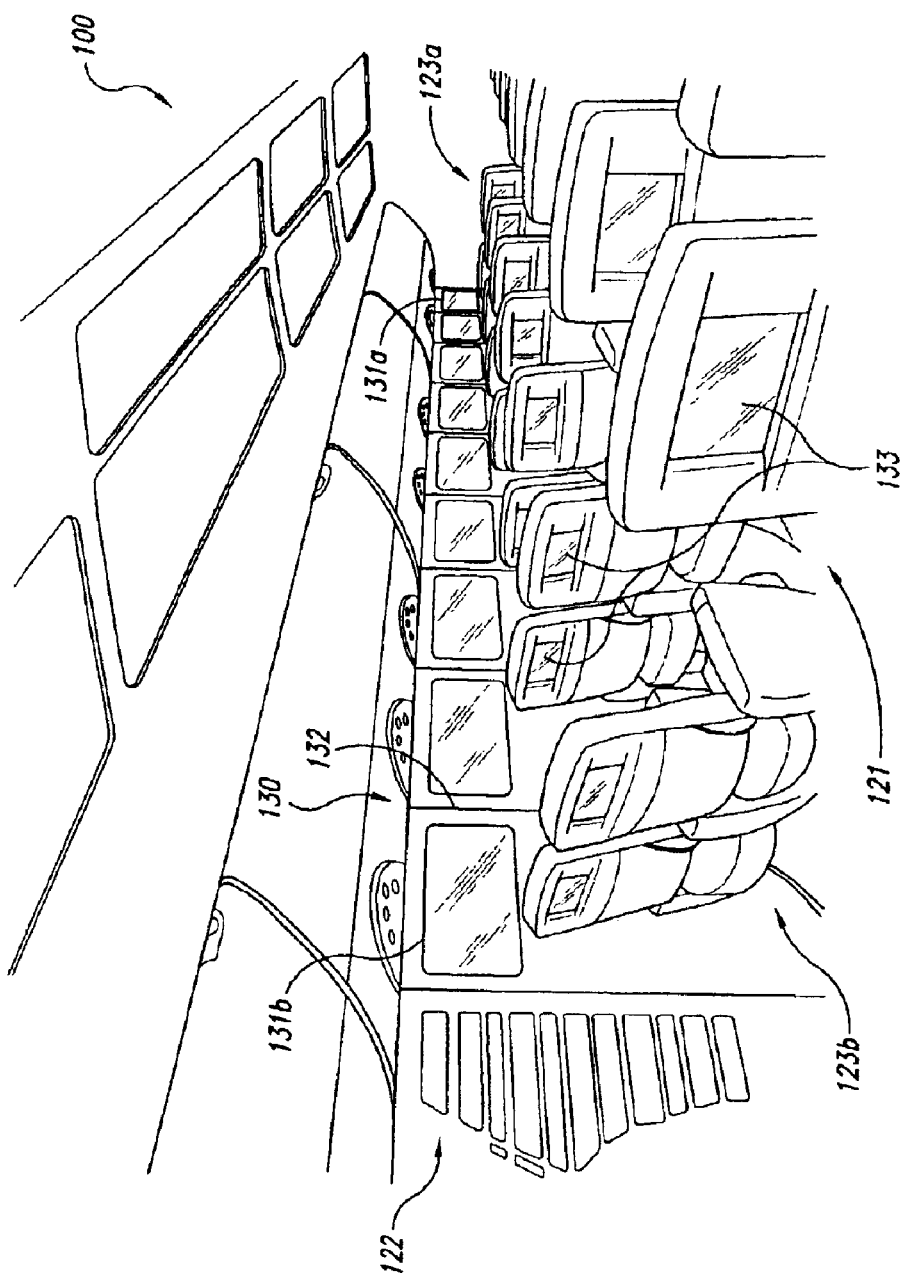
FIG. 5 is a partially schematic, forward-looking isometric illustration of the interior of a portion of an aircraft configured in accordance with an embodiment of the invention.

FIG. 5 is a partially schematic, forward-looking view of a passenger bay 121 configured in accordance with an embodiment of the invention. In one aspect of this embodiment, the passenger bay 121 houses passenger seats 123, which include forward seats 123a and aft seats 123b. The seats 123 can include seat-back displays 133 which present (to the passengers sitting behind them) movies, games, newscasts, safety demonstrations and/or other materials selected by the passengers and/or the crew.

The passenger bay 121 can also include a longitudinally-extending display 130 positioned at least proximate to the partition 122 defining the lateral boundary of the passenger bay 121. In one aspect of this embodiment, the display 130 has display portions 131, including a forward display portion 131a positioned for visual access by passengers seated in the forward seats 123a, and an aft display portion 131b positioned for visual access by passengers in the aft seats 123b. In a further aspect of this embodiment, adjacent display portions 131 can be separated by a separator or partition 132. In other embodiments, adjacent display portions 131b can have no spacing between them. In a particular embodiment, the display 130 can include flexible, polymer screens, and in other embodiments, the display 130 can include other devices configured to present changing images to the passengers.

In any of the foregoing embodiments, the images displayed on the forward display portions 131a and the aft display portion 131b can be representative of the view that a passenger seated in the passenger bay 121 would see if the passenger could look laterally through the fuselage walls to the region external to the aircraft 100. In yet a further aspect of these embodiments, the view at any point in time on the forward display portion 131a can be different than that on the aft display portion 131b to simulate the visual effect a passenger within the passenger bay 121 would feel when looking outside an aircraft that is moving, for example, as the aircraft takes off, lands, and/or taxis. In one embodiment, these images are provided by manipulating signals from cameras that capture the view external to the aircraft, as described in greater detail below with reference to FIGS. 6–8C.

Figure 6:
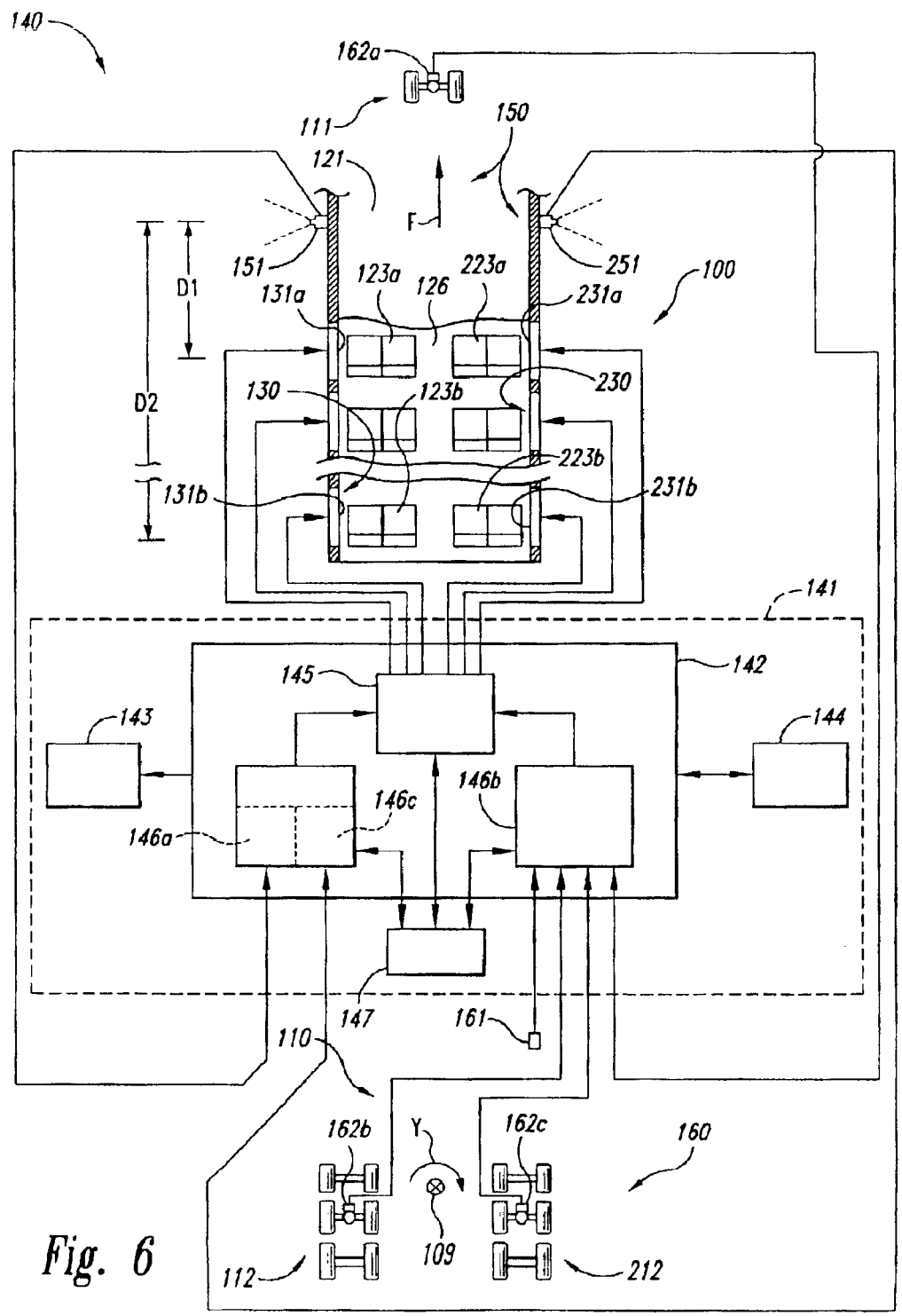
FIG. 6 is a partially schematic block diagram of a system for providing images of a view external to a vehicle in accordance with an embodiment of the invention.

FIG. 6 is a schematic illustration of a system 140 configured to provide passengers seated in different portions of the passenger bay 121 with different views that change in a manner corresponding to the motion of the aircraft 100. The system 140 can include an image gatherer or source 150 (which in turn can include a left camera 151 and a right camera 251) and a plurality of motion sensors 160. A computer 141 can receive signals provided by the image source 150 and the sensors 160. The computer 141 can manipulate the image data received from the image source 150, based upon the signals received from the sensors 160, to provide different images to passengers seated in different seats of the passenger bay 121.

In one embodiment, the passenger bay 121 includes forward left seats 123a and aft left seats 123b positioned on one side of an aisle 126. Forward right seats 223a and aft right seats 223b are positioned on the other side of the aisle 126. A left display 130 is positioned adjacent to the left seats 123, and a right display 230 is positioned adjacent to the right seats 223. The left display 130 can include a first or forward display portion 131a and a second or aft display portion 131b, and the right display 230 can include a first or forward display portion 231a and a second or aft display portion 231b. Each of the displays 130, 230 can present images generated by the image source 150 and processed by the computer 141.

In one embodiment, the left camera 151 is positioned to capture a view looking out from the left side of the aircraft 100, and the right camera 251 is positioned to capture a view looking out from the right side of the aircraft 100. In one aspect of this embodiment, the left and right cameras 151, 251 can be positioned forward of the forward seats 123a, 223a, by a distance D1. In another embodiment, the cameras 151, 251 can be positioned adjacent to or aft of the forward seats 123a, 223a. In any of these embodiments, the aft seats 123b, 223b are located at a different position relative to the cameras 151, 251 than are the forward seats 123a, 223a. For example, in the embodiment shown in FIG. 6, the aft seats 123b, 223b are positioned a distance D2 away from the cameras 151, 251. As the aircraft 100 moves forward (indicated by arrow F) the forward seats 123a, 223a will pass a fixed point on the ground before the aft seats 123b, 223b do. To simulate this effect to the passengers, the system 140 can use data received from the sensors 160 to display the view captured by the cameras 151, 251 on the forward display portions 131a, 231a before displaying the same view on the aft display portions 131b, 231b as described below.

In one embodiment, the sensors 160 can include speed sensors, for example, a central speed sensor 162a positioned at the nose gear 111 to detect a translational speed of the aircraft 100 as it rolls along the ground. In another embodiment, the speed sensor 162a can be positioned on another portion of the landing gear 110 described above with reference to FIG. 3. In a further aspect of this embodiment, the sensors 160 can include a left speed sensor 162b positioned on the left gear 112, and a right speed sensor 162c positioned on the right gear 212. Data from the right and left speed sensors 162b, 162c can be used to determine a turning speed of the aircraft 100 as it moves on the ground, for example, during taxi maneuvers.

The computer 141 can receive signals from the sensors 160 and the image source 150 to present images at different times to different passengers in the aircraft 100. In one embodiment, the computer 141 includes a processor 142 configured to process the signals received from the sensors 160 and direct signals to the displays 130, 230. The computer 141 can include a system I/O portion 144 (such as a keyboard) to allow inputs to the system 140, and a diagnostic system display 143 to provide status signals corresponding to the operation of the system 140. In one embodiment, the processor 142 can include a first signal receiving portion 146a configured to receive signals from the left camera 151, a second signal receiving portion 146b configured to receive signals from the sensors 160, and a third signal receiving portion 146c configured to receive signals from the right camera 251. Data can be stored and retrieved from a memory 147. A signal processing portion 145 can receive the signals corresponding to the images transmitted by the cameras 151, 251 and can transmit output signals corresponding to images that change with time (depending on which display portion 131 the signal is transmitted to) based on the signal(s) received from one or more of the sensor(s) 160.

In one example, the signal processing portion 145 can delay the transmission of the image signals to the first display portions 131a, 231a by a time corresponding to the distance D1 divided by the speed of the aircraft 100. The signal processing portion 145 can delay the transmission of the images to the second display portions 131b, 231b by a time corresponding to the distance D2 divided by the speed of the aircraft 100. Display portions between the first display portions 131a, 231a and the aft display portions 131b, 231b can receive image signals delayed by time factors that correspond to the distances between these display portions and the relevant camera 151, 251. If D1 or D2 is zero, the transmission of the image to the corresponding display need not be delayed. If the camera (e.g., the right camera 151) is positioned between the first and second display portions, (e.g., between the first display portion 131a and the second display portion 131b), then the image transmitted to the first display portion 131a need not be delayed, and the image transmitted to the second display portion 131b can be delayed by (D1+D2) divided by the speed of the aircraft 100. In other embodiments, the delay can be computed in other manners that also account for the motion of the aircraft 100.

In another embodiment, the signal processing portion 145 can account not only for linear translation of the aircraft 100, but also for rotation of the aircraft 100 about a yaw axis 109 which is perpendicular to the plane of the passenger bay 121. In a particular aspect of this embodiment, the signal processing portion 145 can determine the relative difference between motion detected by the left speed sensor 162b and the motion detected by the right speed sensor 162c to determine a turning rate of the aircraft 100. The signal processing portion 145 can then delay or otherwise manipulate the images presented to the displays 130, 230 in a manner that reflects the fact that the line of sight from the forward seats 123a, 223a will sweep over a fixed ground point at a different time than will a line of sight from the aft seats 123b, 223b. This effect may occur when the aircraft 100 is only rotating about the yaw axis 109 (as indicated by arrow Y), and/or when the aircraft 100 is both rotating about the yaw axis and translating, as indicated by arrow F.

In a particular embodiment, the cameras 151, 251 can transmit streams of digital images that are stored or cached in the computer memory 147. Each display portion 131 can have associated with it a register that represents the delay factor (e.g., the distance between the display portion 131 and the relevant camera) corresponding to that display portion 131. Each display portion 131 can also have associated with it a register corresponding to the relevant camera for that display portion 131. The processing portion 145 can sample the digitally stored images and apply to the transmission of each image a delay that corresponds to the appropriate delay factor and the speed of the aircraft 100. Accordingly, the processing portion 145 can transmit the stored images at different times for different display portions.

One feature of an embodiment of the system 140 described above is that it can provide an image to the forward seats 123a, 223a before providing the same image to the aft seats 123b, 223b. An advantage of this arrangement is that it can more accurately simulate what passengers would actually see if they were able to have visual access to the region directly outside the aircraft. A particular advantage of this arrangement is that a passenger who has visual access to a greater portion of the displays 130, 230 than is immediately adjacent his or her seat (e.g., a passenger walking along the aisle 126 or a passenger looking across the aisle 126) will receive views that appear to pass along the displays 130, 230 from front to back as the aircraft 100 moves forward. The motion of these views will be consistent with the motion that the passenger feels. By making the view the passenger sees consistent with the motion the passenger feels, the passenger may be less susceptible to motion sickness.

The advantages described above can be particularly apparent when the system 140 simulates the motion of the aircraft 100 relative to objects that are close by. For example, when the aircraft 100 is on the ground, other ground-based objects appear to pass by the aircraft 100 at a relatively great speed. When the aircraft 100 is airborne, such objects are distant and accordingly, the difference between what a passenger at the forward part of the aircraft 100 would see and what a passenger at the aft part of the aircraft 100 would see do not significantly differ. Accordingly, in a further embodiment, the image presented at the first display portion 131a can be synchronized with the image presented at the second display portion 131b, and the image presented at the first display portion 231a can be synchronized with the image presented at the second display portion 231b after the aircraft 100 has become airborne. In a particular embodiment, the sensors 160 can include a wheels-up sensor 161 which detects the point at which the aircraft 100 leaves the ground and the point at which the landing gear 110 are deployed. The foregoing images can be synchronized when the wheels-up sensor 161 detects that the gear 110 leave the ground after take off (or optionally, after a delay period from this time) and the images can be de-synchronized during landing approach when the landing gear 110 are deployed. In other embodiments, other signals can be used to synchronize and/or de-synchronize the images, or the images can remain de-synchronized for the entire flight.

In other embodiments, the system 140 can have other arrangements. For example, in one embodiment, only a portion of the passenger bay 121 may not have direct visual access to the region exterior to the aircraft 100. For example, the right seats 223a, 223b may be positioned adjacent to windows, while the left seats 123a, 123b may not. In this embodiment, the right camera 251 and the third signal receiving portion 146c can be eliminated. Optionally, the second signal receiving portion 146b can receive a signal corresponding only to the translational motion of the aircraft 100 and not the rotational motion of the aircraft 100. In other embodiments, the system 140 can have other arrangements that also process the received image signals in a manner to simulate the motion of the aircraft 100. In any of these embodiments, the signal received can be a digital signal or an analog signal. In a particular embodiment, the signal received can be a streaming digital image signal.

Figure 7:
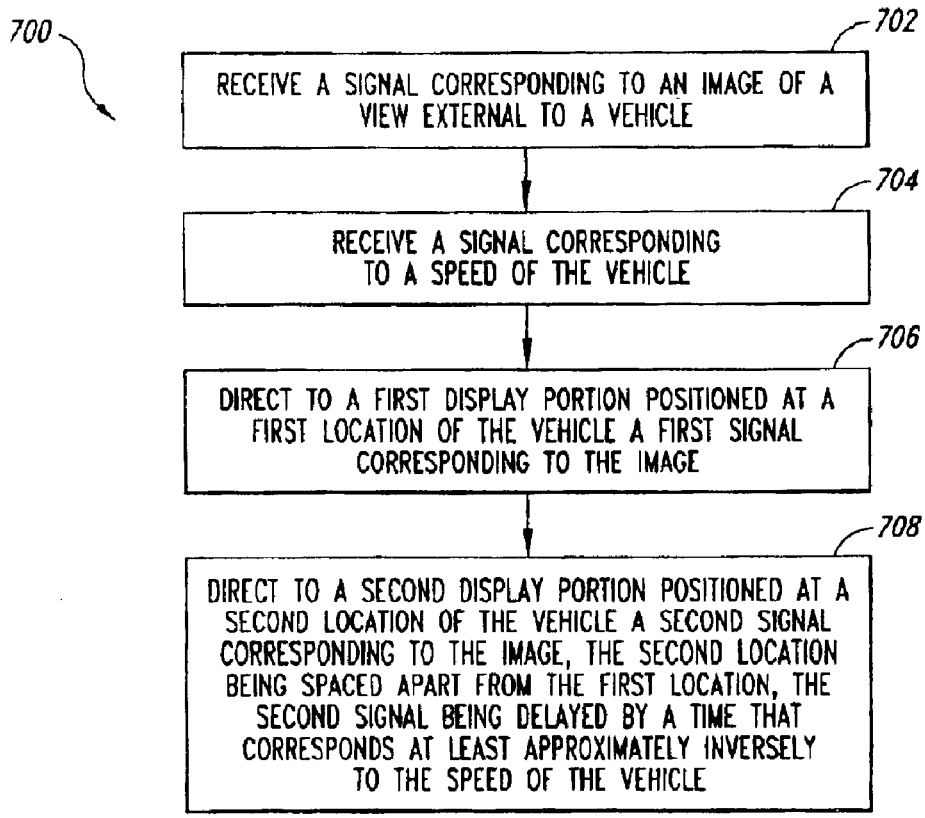
FIG. 7 is a flow chart illustrating a method for presenting an image of a view external to a vehicle in accordance with an embodiment of the invention.
Figure 8A:
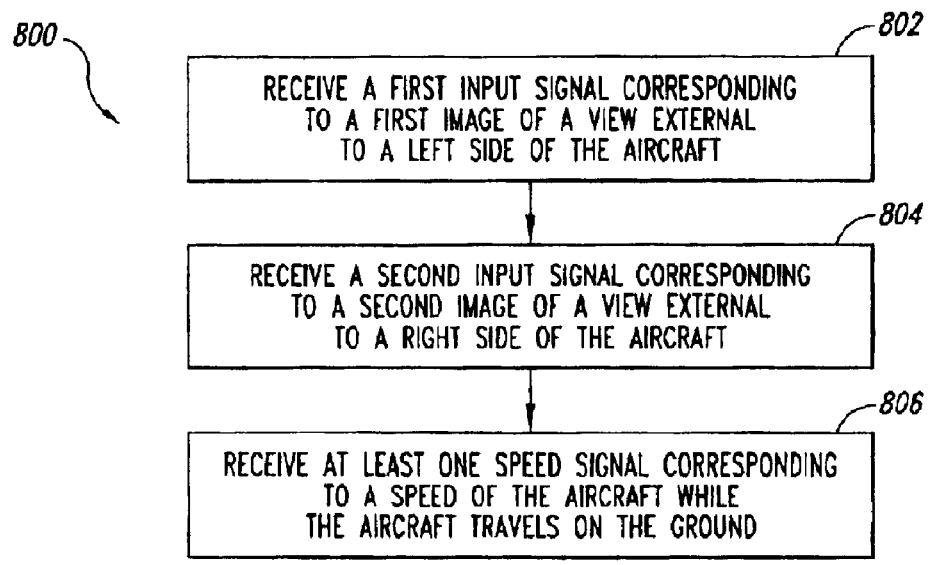
FIGS. 8A–8C are flow charts illustrating methods for presenting images of views external to vehicle in accordance with further embodiments of the invention.
Figure 8B:
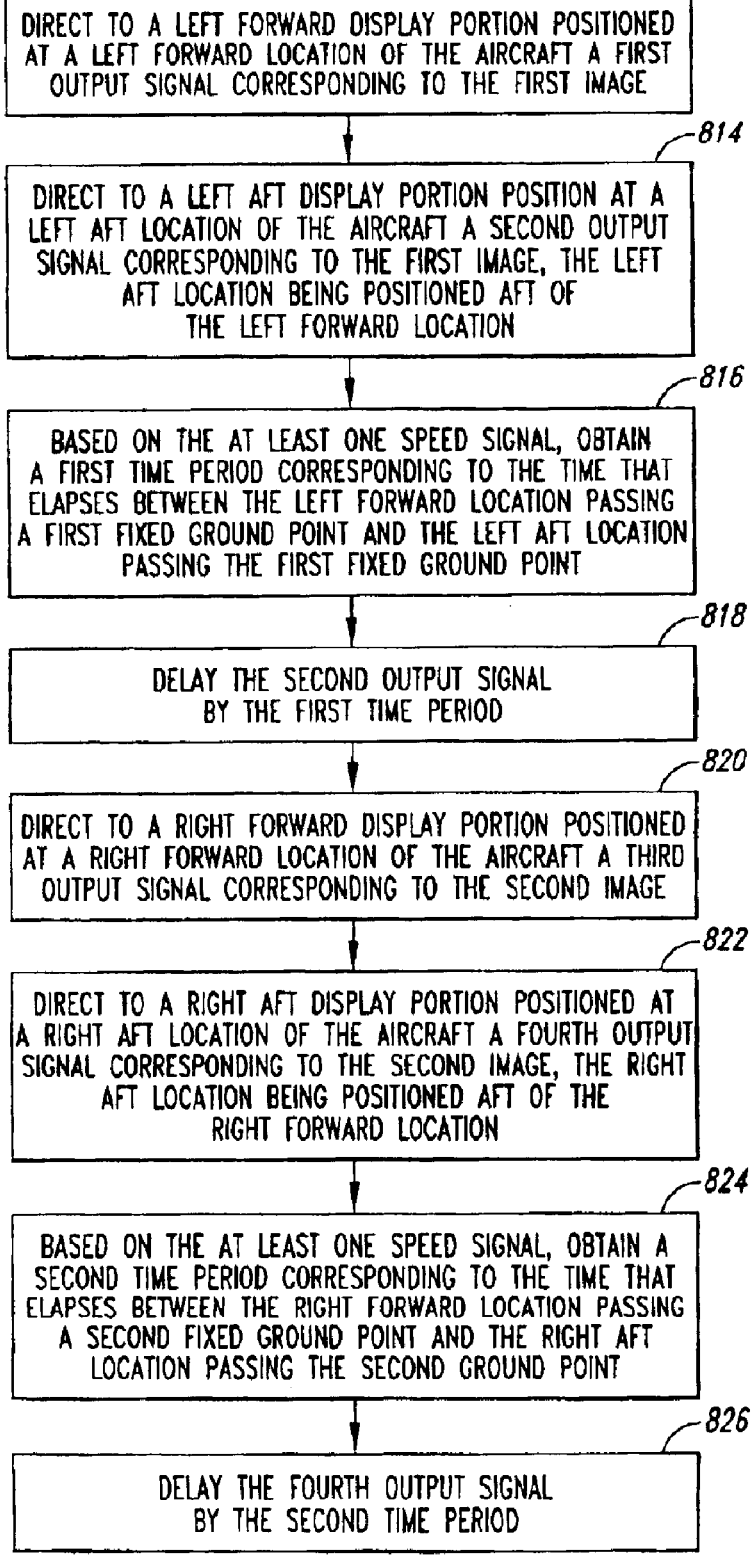
Figure 8C:
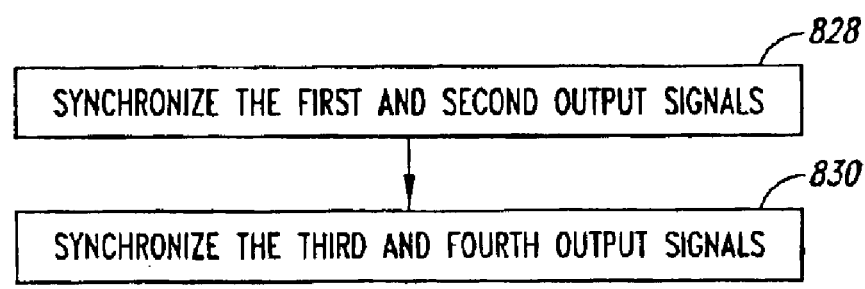

FIGS. 7–8C are flow diagrams illustrating methods or processes performed in accordance with embodiments of the invention. A process 700 shown in FIG. 7 includes receiving a signal corresponding to an image of a view external to a vehicle (process portion 702) and receiving a signal corresponding to a speed of the vehicle (process portion 704). In process portion 706, the method includes directing to a first display portion positioned at a first location of the vehicle a first signal corresponding to the image, and in process portion 708, the method includes directing to a second display portion positioned at a second location of the vehicle a second signal corresponding to the image, with the second location being spaced apart from the first location and with the second signal delayed by a time that corresponds at least approximately inversely to the speed of the vehicle.

FIGS. 8A–8C illustrate portions of a process 800 that provides different signals to left and right locations of an aircraft 100 and accounts for aircraft take-off and landing. Beginning with FIG. 8A, the process 800 can include receiving a first input signal corresponding to a first image of a view external to the left side of the aircraft (process portion 802) and receiving a second input signal corresponding to a second image of a view external to the right side of the aircraft (process portion 804). The process 800 can further include receiving at least one speed signal corresponding to a speed of the aircraft 100 while the aircraft 100 travels on the ground (process portion 806).

FIG. 8B illustrates process portions completed in accordance with one embodiment of the invention while the aircraft 100 travels on the ground. For example, process portion 812 includes directing to a left forward display portion positioned at a left forward location of the aircraft a first output signal corresponding to the first image. Process portion 814 includes directing to a left aft display portion positioned at a left aft location of the aircraft a second output signal corresponding to the first image, with the left aft location being positioned aft of the left forward location. Based on the at least one speed signal, the method further includes obtaining a first time period corresponding to the time that elapses between the left forward location passing a first fixed ground point and the left aft location passing the first fixed ground point (process portion 816) and then delaying the second output signal by the first time period (process portion 818). A series of process portions similar to process portions 812–818 can be completed for the right forward and aft display portions, as indicated by process portions 820–826. Accordingly, a third output signal can be directed to a right forward display portion and a fourth output signal can be directed to the right aft display portion, with the fourth output signal delayed by a second time period.

Referring now to FIG. 8C, when the aircraft 100 leaves the ground, the first and second output signals (directed to the left forward and left aft display portions, respectively) can be synchronized in process portion 828. The third and fourth output signals (directed to the right forward display portion and the right aft display portion, respectively) can be synchronized in process portion 830.

From the foregoing, it will be appreciated that specific embodiments of the invention have been described herein for purposes of illustration, but that various modifications may be made without deviating from the spirit and scope of the invention. Accordingly, the invention is not limited except as by the appended claims.

I claim:

1. A system for processing images corresponding to a view external to a vehicle, comprising:
   a first signal receiving portion configured to receive a signal corresponding to an image of a view external to a vehicle;
   a second signal receiving portion configured to receive a signal corresponding to a speed of the vehicle; and
   a signal processing portion configured to:
      direct to a first display portion positioned at a first location of the vehicle a first signal corresponding to the image;
      direct to a second display portion positioned at a second location of the vehicle a second signal corresponding to the image, the second location being different than the first location; and
      delay the second signal by a time that corresponds at least approximately inversely to the speed of the vehicle.

2. The system of claim 1 wherein the first signal receiving portion is configured to receive a streaming digital image of the view external to the vehicle.

3. The system of claim 1, further comprising the first and second display portions.

4. The system of claim 1 wherein the signal processing portion includes a computer processor.

5. The system of claim 1, further comprising the first and second display portions, and wherein the first and second display portions are part of a generally continuous panel.

6. The system of claim 1, further comprising a camera operatively coupled to the first receiving portion to transmit the signal corresponding to the image of the view external to the vehicle.

7. The system of claim 1, further comprising a speed sensor operatively coupled to the second signal receiving portion to transmit the signal corresponding to the speed of the vehicle.

8. The system of claim 1, further comprising at least one speed sensor operatively coupled to the second signal receiving portion to transmit the signal corresponding to the speed of the vehicle, and wherein the signal corresponds to a turning speed of the vehicle.

9. The system of claim 1 wherein the vehicle includes at least one first wheel and at least one second wheel spaced laterally apart from the at least one first wheel and wherein the system further comprises:
    a first speed sensor operatively coupled to the at least one first wheel to detect a speed of the at least one first wheel; and
    a second speed sensor operatively coupled to the at least one second wheel to detect a speed of the at least one second wheel.

10. The system of claim 1 wherein the vehicle includes an aircraft and wherein the signal processing portion is configured to synchronize the first and second signals when the aircraft is airborne.

11. A system for processing images corresponding to a view external to a vehicle, comprising:
    first signal receiving means for receiving a signal corresponding to a view external to a vehicle;
    second signal receiving means for receiving a signal corresponding to a speed of the vehicle; and
    signal processing means for processing the first and second signals, the signal processing means being configured to:
        direct to a first display portion positioned at a first location of the vehicle a first signal corresponding to the image;
        direct to a second display portion positioned at a second location of the vehicle a second signal corresponding to the image, the second location being different than the first location; and
        delay the second signal by a time that corresponds at least approximately inversely to the speed of the vehicle.

12. The system of claim 11 wherein the first signal receiving means are configured to receive a streaming digital image of the view external to the vehicle.

13. The system of claim 11, further comprising the first and second display portions.

14. The system of claim 11 wherein the signal processing means include a computer processor.

15. The system of claim 11, further comprising the first and second display portions, and wherein the first and second display portions are part of a generally continuous panel.

16. The system of claim 11, further comprising image gathering means for gathering the image of the view external to the vehicle, the image gathering means being coupled to the first receiving means to transmit the signal corresponding to the image of the view.

17. The system of claim 11, further comprising speed sensor means for detecting the speed of the vehicle, the speed sensor means being operatively coupled to the second signal receiving means to transmit the signal corresponding to the speed of the vehicle.

18. The system of claim 11, further comprising speed sensor means for detecting a turning speed of the vehicle, the speed sensor means being operatively coupled to the second signal receiving portion to transmit the signal corresponding to the speed of the vehicle.

* * * * *

UNITED STATES PATENT AND TRADEMARK OFFICE
CERTIFICATE OF CORRECTION

PATENT NO.        : 7,088,310 B2                                   Page 1 of 1
APPLICATION NO.   : 10/427677
DATED             : August 8, 2006
INVENTOR(S)       : William C. Sanford It is certified that error appears in the above-identified patent and that said Letters Patent is hereby corrected as shown below:

Front Page (56)
References Cited, Please insert the following cited references that were filed with September 23, 2005 and acknowledged by the Examiner October 5, 2005:

| | | |
|---|---|---|
| --US-20040217976-A1 | 11-04-2004 | Sanford; |
| US-20040217978-A1 | 11-04-2004 | Humphries; |
| US-5,031,860 | 07-16-1991 | Ruiz et al.; |
| US-5,499,120 | 03-12-1996 | Hansen; |
| US-6,102,332 | 08-15-2000 | Haxton et al.; |

OTHER PUBLICATIONS
http://www.tvphotography.com/fleetweek.htm, Called C-2 (4pgs);--

Signed and Sealed this

Fourteenth Day of November, 2006

JON W. DUDAS
*Director of the United States Patent and Trademark Office*